(12) United States Patent
Ratcliffe

(10) Patent No.: US 7,900,498 B1
(45) Date of Patent: Mar. 8, 2011

(54) CALIBRATED IMPACT HAMMER

(75) Inventor: Colin P. Ratcliffe, Millersville, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 377 days.

(21) Appl. No.: 11/765,588

(22) Filed: Jun. 20, 2007

Related U.S. Application Data

(60) Provisional application No. 60/806,338, filed on Jun. 30, 2006.

(51) Int. Cl.
*G01P 15/09* (2006.01)
*G01P 15/00* (2006.01)

(52) U.S. Cl. ............... 73/12.09; 73/12.01; 73/12.04; 73/12.07

(58) Field of Classification Search ...... 73/12.01–12.09, 73/12.11, 12.12
See application file for complete search history.

(56) References Cited

U.S. PATENT DOCUMENTS

| | | | | |
|---|---|---|---|---|
| 4,615,209 A | * | 10/1986 | Change, Jr. | 73/12.09 |
| 4,682,490 A | * | 7/1987 | Adelman et al. | 73/12.09 |
| 4,799,375 A | * | 1/1989 | Lally | 73/12.09 |
| 5,662,175 A | * | 9/1997 | Warrington et al. | 173/132 |
| 5,663,894 A | * | 9/1997 | Seth et al. | 702/56 |
| 5,686,652 A | * | 11/1997 | Pfund | 73/12.04 |
| 5,983,701 A | * | 11/1999 | Hassani et al. | 73/12.01 |
| 6,684,681 B1 | * | 2/2004 | Zombo | 73/12.11 |
| 6,859,674 B1 | * | 2/2005 | Seth et al. | 700/97 |

* cited by examiner

*Primary Examiner* — Lisa M Caputo
*Assistant Examiner* — Jonathan Dunlap
(74) *Attorney, Agent, or Firm* — Amy Ressing; Suresh Koshy

(57) ABSTRACT

An apparatus includes a positioner. The apparatus includes a striker axially movable in the positioner. The striker includes a striker inner end. The apparatus includes a force gauge axially movable in the positioner. The force gauge includes a force gauge inner end. The force gauge inner end is in communication with the striker inner end. Optionally, the striker defines at least one fluid passage axially therethrough.

14 Claims, 4 Drawing Sheets

CALIBRATED IMPACT HAMMER

This application claims the benefit of U.S. Provisional Application Ser. No. 60/806,338 filed Jun. 30, 2006 and is incorporated by reference herein in its entirety.

TECHNICAL FIELD

This invention relates generally to an exciter, and, more particularly, to a calibrated impact hammer.

BACKGROUND ART

There are many situations where structures need to be excited in order to measure their vibration characteristics. Normally, theses structures are tested in air. For situations to where the structures are tested in air, a common exciter is a calibrated impact hammer. For underwater applications, waterproofing provides an exciter that survives the environment. For example, a sledge-type calibrated impact hammer is used for underwater applications.

DISCLOSURE OF THE INVENTION

Applicant determined that underwater use of a conventional sledge-type hammer is undesirable for at least three reasons. First, use of such a hammer is physically hard work for the operator/diver. Second, in practice, it is difficult for the operator/diver to ensure repeated excitation at a same precise location. Third, in practice, it is difficult for the operator/diver to deliver consistent, substantially identical, excitations.

An embodiment of the present invention includes an underwater exciter that is easier to use, both in terms of physical effort required by the operator, and ability to excite precise location.

An embodiment of the invention includes an exciter, or "hammer." For example, the exciter provides a measured single pulse of force excitation at a precise location, with minimal effort. Optionally, the design of the exciter reflects underwater applications. Optionally, the exciter could also be used for in-air applications, under wet conditions to (e.g., rain). Optionally, the exciter is used in more conventional environments, such as in air. For example, cost can be saved by having a version that is not waterproofed, in which case application is limited to dry conditions.

An embodiment of the invention includes an apparatus. The apparatus includes a positioner. The apparatus includes a striker axially movable in the positioner, the striker including a striker inner end. The apparatus includes a force gauge axially movable in the positioner, the force gauge including a force gauge inner end, the force gauge inner end being in communication with the striker inner end.

Optionally, the positioner includes a fixed and/or interchangeable tip proximate to the force gauge inner end.

Optionally, the apparatus further includes at least one pulse shaping tip, the force gauge including a force gauge outer end, the at least one pulse shaping tip being in communication with at least one of the force gauge inner end and the force gauge outer end. Optionally, the at least one pulse shaping tip includes a first pulse shaping tip and a second pulse shaping tip, the first pulse shaping tip being in communication with the force gauge inner end, the second pulse shaping tip being in communication with the force gauge outer end. Optionally, the first pulse shaping tip includes a first hardness, the second pulse shaping tip comprises a second hardness, the second hardness being one of lesser, equal to, and greater than the first hardness.

Optionally, the apparatus further includes an actuator operatively connected to the striker. Optionally, the actuator is a mechanical actuator and/or an electrical actuator. Optionally, the mechanical actuator includes a handle, a spring-latch-button actuator, a gravity actuator, a pneumatic actuator, a pyrotechnic actuator, a hydraulic actuator, and/or a cam-piston actuator. Optionally, the electrical actuator includes a linear shaft actuator. Optionally, the linear shaft actuator includes a solenoid, a linear coil actuator, and/or a linear magnet.

Optionally, the apparatus further includes a processor in communication with the force gauge, and a vibration sensor in communication with the processor.

Optionally, the striker defines at least in part at least one fluid passage axially therethrough. Optionally, the positioner and the striker define the at least one fluid passage.

BEST MODES OF CARRYING OUT THE INVENTION

Figure 1:
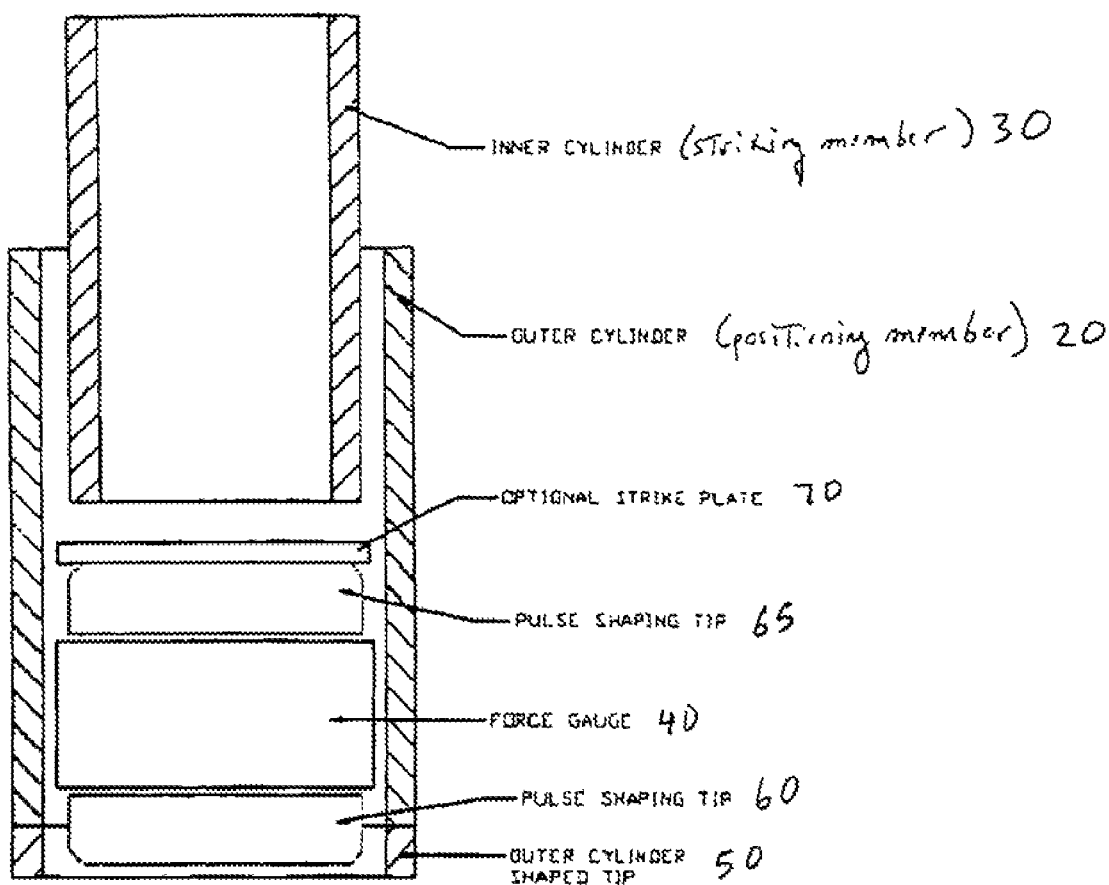
FIG. 1 is a cross-sectional view of an illustrative embodiment of the present invention.

An embodiment of the invention includes a hammer 10 and is described relative to FIG. 1. The hammer 10 includes a positioner 20. The hammer includes a striker 30 axially movable in the positioner 20, the striker including a striker inner end. The hammer 10 includes a force gauge 40 axially movable in the positioner 20. The force gauge 40 includes a force gauge inner end, the force gauge inner end being in communication with the striker inner end.

Optionally, the positioner 20 includes a fixed and/or interchangeable tip 50 proximate to the force gauge inner end.

Optionally, the hammer further includes at least one pulse shaping tip 60, 65. The force gauge 40 includes a force gauge outer end. The at least one pulse shaping tip 60, 65 is in communication with at least one of the force gauge inner end and the force gauge outer end. Optionally, the at least one pulse shaping tip 60, 65 includes a first pulse shaping tip 60 and a second pulse shaping tip 65, the first pulse shaping tip 60 being in communication with the force gauge inner end, the second pulse shaping tip 65 being in communication with the force gauge outer end. Optionally, the first pulse shaping tip 60 includes a first hardness, the second pulse shaping tip 65 comprises a second hardness, the second hardness being lesser, equal to, or greater than the first hardness.

Figure 2:
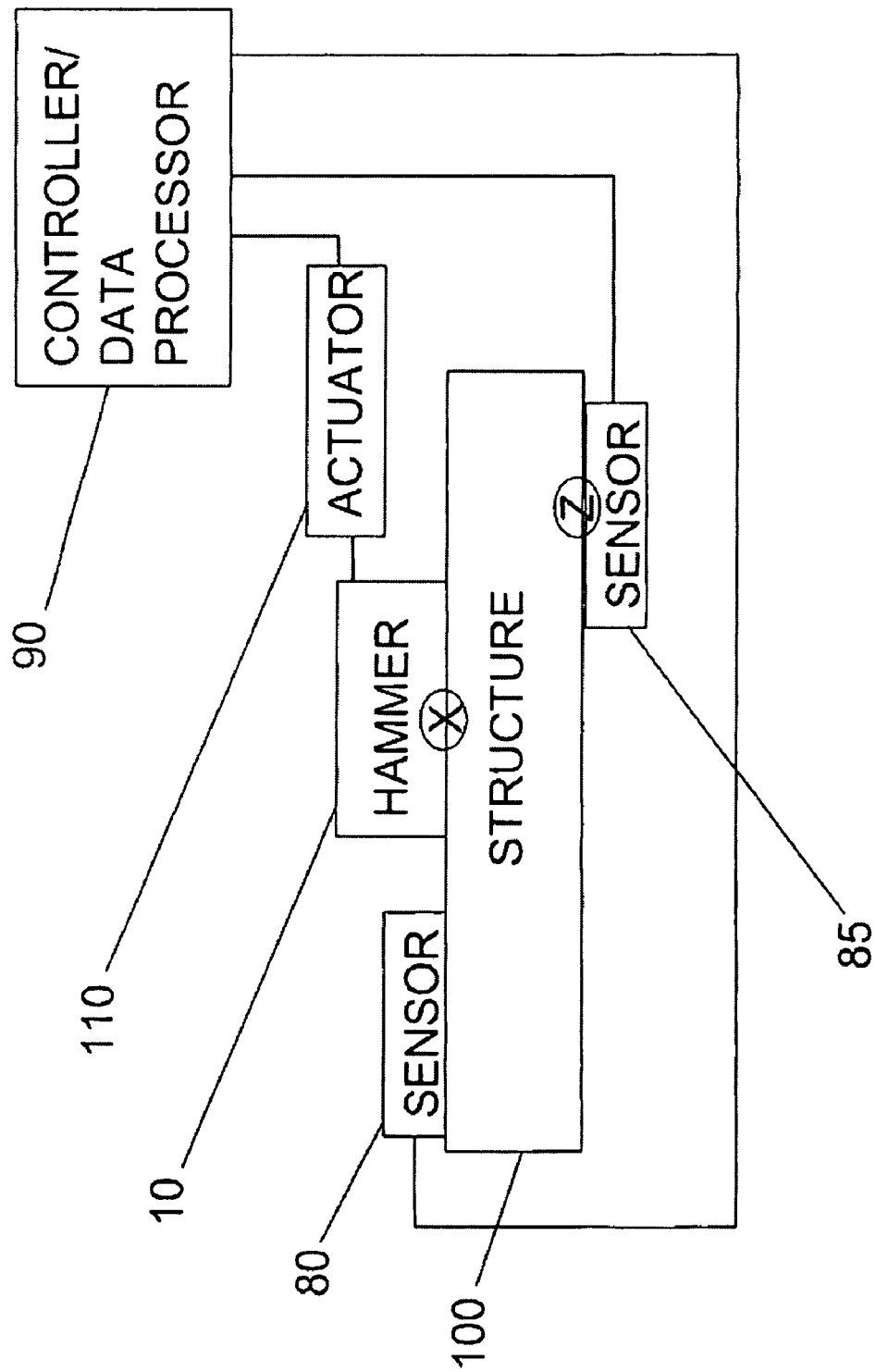
FIG. 2 is a block diagram of an illustrative system incorporating an embodiment of the present invention.
Figure 3A:
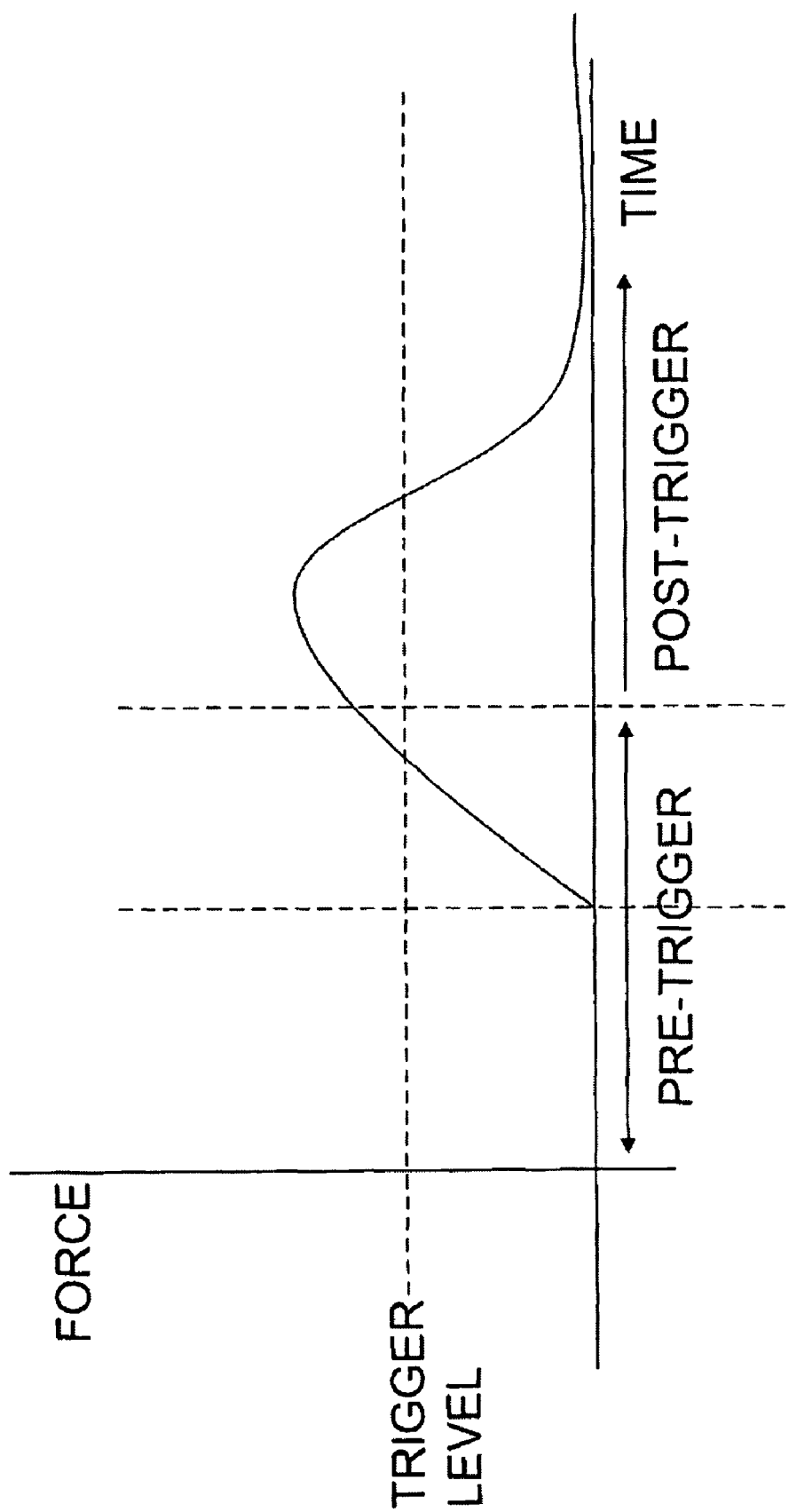
FIG. 3a is an illustrative input waveform representing a strike by an embodiment of the present invention.
Figure 3B:
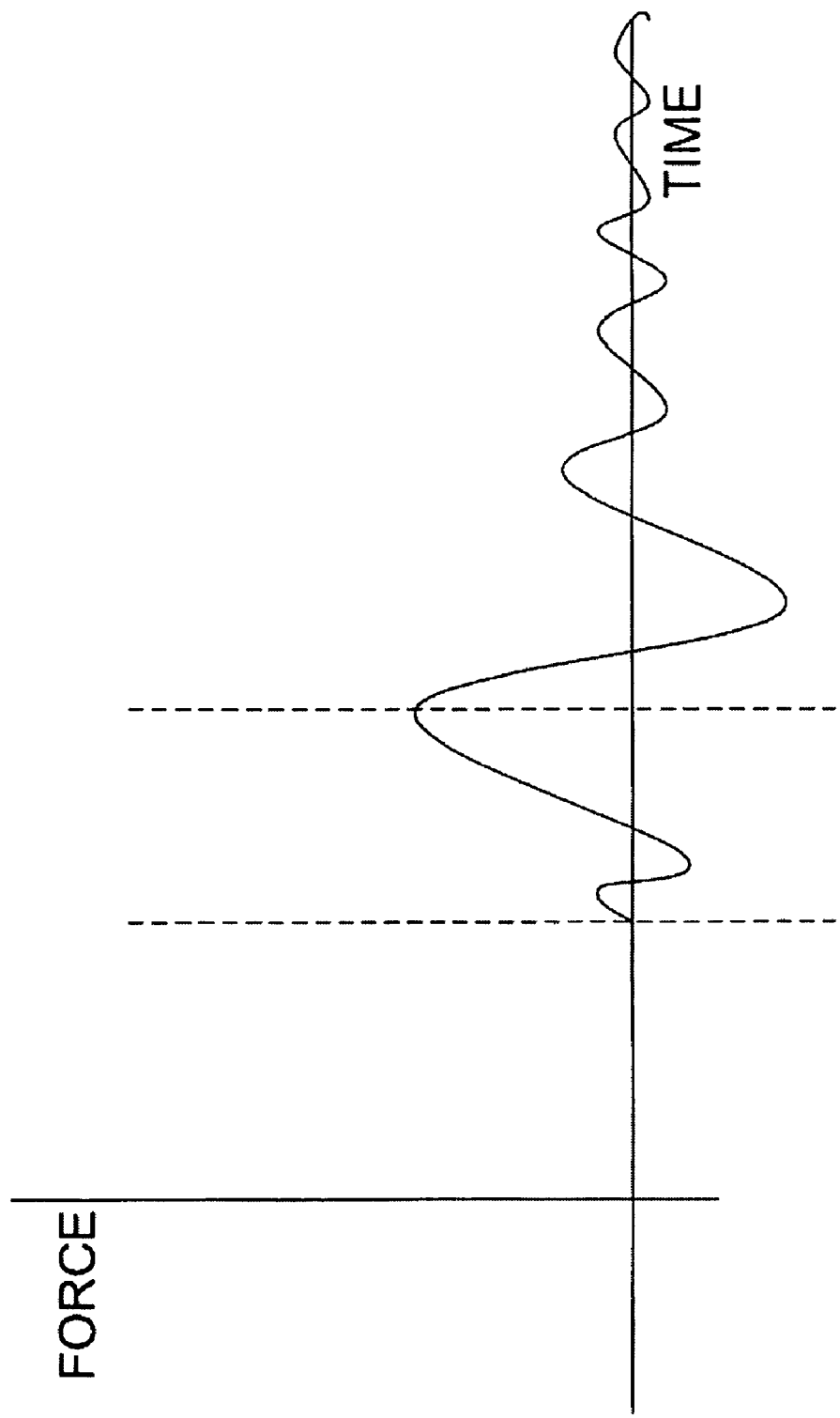
FIG. 3b is an illustrative response waveform caused by the strike of an embodiment of the present invention.

Optionally, as shown by way of illustration in FIG. 2, the hammer 10 further includes an actuator 110 operatively connected to the striker 30. Optionally, the actuator 110 is a mechanical actuator and/or an electrical actuator. Optionally, the mechanical actuator includes a handle, a spring-latch-button actuator, a gravity actuator, a pneumatic actuator, a pyrotechnic actuator, a hydraulic actuator, and/or a cam-piston actuator. Optionally, the electrical actuator includes a linear shaft actuator. Optionally, the linear shaft actuator includes a solenoid, a linear coil actuator, and/or a linear magnet.

Optionally, the hammer 10 further includes a processor 90 in communication with the force gauge 40, and at least one vibration sensor 80, 85 in communication with the processor.

Another embodiment of the invention is described relative to FIGS. 1 and 2. The hammer 10 includes, for example, a plurality of prismatic elongated shapes, wherein at least one fits within another. In an exemplary embodiment as discussed in more detail below, the invention includes at least two concentric cylinders. The shapes optionally comprise corrosion-resistant material for underwater use. This embodiment includes a positioning member 20, a striking member 30, and a force gauge 40.

The positioning member 20 performs as follows. The operator of the hammer 10 optionally uses the positioning member 20 to position the hammer against the structure 100 under test. The base of the positioning member optionally includes a fixed or interchangeable tip 50. For example, a plurality of interchangeable tips includes different shapes that ensure good contact with the structure 100 under test. For example, the tip shape includes a tripod-like base for flattish structures or a 2-sided rail for structures with a single axis of curvature. Specialist bases for any test structure are optionally provided. The positioning member 20 holds a force gauge 40 close to or touching the structure 100.

The force gauge 40 is, for example, any device that dynamically measures force. Nonlimiting principles of operation of the force gauge 40 include the strain gauge principle or the piezoelectric principle. For underwater applications, the force gauge 40 is optionally fully waterproofed. For example, the force gauge 40 includes a bonded cable or cables.

The force gauge 40 is disposed in the positioning member 20 so as to maintain gauge functionality. That is, a force gauge will only operate, if it can move a "little" bit. For example, the force gauge 40 is disposed in the positioning member 20 with a flexible bonding material to permit sufficient axial motion for the gauge to function correctly, and/or through a mechanical constraint that also permits this motion.

One or more pulse shaping tips 60, 65 are optionally fitted on either or both sides of the force gauge 40. Optionally, a strike plate 70 communicates with the pulse shaping tip 60. For example, the different tips 60, 65 have different hardnesses such that a single hammer or exciter is optionally modified by the operator to provide pulses of varying shapes, amplitudes, and durations. Such selection is, for example, made by the operator in the field. Tips 60, 65 are optionally attached to the force gauge 40. Non-limiting examples of modes of attachment include screwing, gluing, welding, etc. For example, if an embodiment of the invention includes an upper pulse shaping tip between the striking member 30 and the force gauge 40 and includes a lower pulse shaping tip at another end of the force gauge, then the lower pulse shaping tip is optionally harder than the upper pulse shaping tip to limit travel of the force gauge 40.

The striking member 30 is optionally designed with specific mass to achieve a predetermined level of excitation and is described by way of illustration as follows. The striking member 30 moves inside the positioning member 20. As the striking member 30 moves down the positioning member 20, any fluid inside the device can move about this striking member, thereby offering minimal resistance. This reduces operator fatigue and offers improved repeatability when using the hammer 10.

The inner end of the striking member 30 impacts the force gauge 40 or any pulse shaping tip 60 communicating with the force gauge 40.

The mass of the striking member 30 is optionally predetermined to achieve a predetermined amount of excitation energy. In general, the heavier the striking member 30, the greater the energy level of the vibration detected or sensed. Extra masses are optionally connected to the striking member 30 to vary the excitation energy.

The outer end of the striking member 30 is optionally modified to include a handle. The operator optionally uses this handle, or holds the side or end of the positioning member 20, depending upon ease of use.

In another embodiment, the hammer 10 includes a striking member 30 operated in full or in part by a mechanical and/or electrical actuator 110. Actuation is optionally accomplished manually. Non-limiting examples of manual actuators include a handle, a spring-latch-button system, a gravity actuator, a pneumatic actuator, a pyrotechnic actuator, a hydraulic actuator, a cam-piston system. Actuation is optionally accomplished electrically, for example, with a solenoid.

Alignment of the striking member 30 within the positioning member 20 is optionally accomplished by having shaping on the outside of the striking member. Non-limiting examples of such shaping include riders, cams, and non-circular bearing type surfaces. Such shapes are optionally of the same material as the striking member 30, or are formed from a different bearing material.

Distributed contact between the striking member 30 and the force gauge 40 is ensured either by having the end of the striking member be closed across, but with one or more openings to permit fluid (e.g., air or water) flow through it such as a honeycombed shape. For example, the striking member 30 defines at least in part one or more fluid passages axially therethrough, permitting fluid flow through or around the striking member. For example, the striking member 30 and the positioning member 20 together define one or more fluid passages. Alternatively, the hammer 10 includes a striking plate 70 on the gauge 40 or pulse shaping tip 60.

A capture system prevents the parts of the device from separating. Non-limiting examples of which include projections riding in slots, or some other means.

Illustrative Operation

The operator selects the appropriate pulse shaping tip(s) 60, 65, depending upon the structure 100 under test and the test specifications.

As illustrated in attached FIG. 2, the device is placed, for example, at position X against the structure to be tested.

The operator actuates the hammer 10. The striking member 30 hits the force gauge 40 or its pulse shaping tip 60, 65. The force is measured by the force gauge 40, and is then transmitted though the force gauge onto the structure 100. The structure's response is detected by detectors 80, 85 (for example, at position Z). Data from the force gauge 40 and the detectors 80, 85 are supplied to a controller/data processor 90 for processing.

Obviously, many modifications and variations of the present invention are possible in light of the above teachings without departing from the true scope and spirit of the invention. It is therefore to be understood that the scope of the invention should be determined by referring to the following appended claims.

What is claimed is:

1. A method comprising:
providing a calibrated impact hammer, wherein the calibrated impact hammer comprises a positioner; a striker axially movable in the positioner, the striker comprising a striker inner end; a force gauge axially movable in the positioner, the force gauge comprising a force gauge inner end, the force gauge inner end being in communication with the striker inner end, at least one of the positioner and the striker comprising a fluid passage axially therethrough, holding the positioner under water against an underwater structure whose vibration characteristics are to be measured;

applying the striker under water to hit a location on the structure such that water flows one of through and around the striker; and repeating said applying the striker step to hit the location repeatedly.

2. The method according to claim 1, wherein the force gauge comprises a force gauge outer end, the calibrated hammer further comprising at least one of a first pulse shaping tip in communication with the striker inner end and the force gauge inner end and a second pulse shaping tip in communication with the force gauge outer end.

3. The method according to claim 2, wherein the calibrated hammer further comprises a strike plate in communication with the striker inner end and the first pulse shaping tip.

4. The method according to claim 1, wherein the positioner comprises one of a fixed tip and a plurality of interchangeable tips to ensure contact between the positioner and the structure.

5. The method according to claim 1, wherein the calibrated impact hammer further comprises one of a mechanical actuator and an electrical actuator connected to the striker, wherein said applying the striker step comprises actuating one of the mechanical actuator and the electrical actuator.

6. The method according to claim 1, further comprising:
providing a processor;
providing at least one vibration sensor communicating with the processor and the force gauge, the at least one vibration sensor measuring the vibration characteristics of the underwater structure.

7. The method according to claim 1, wherein the force gauge is waterproofed and is one of a strain gauge-type force gauge and a piezo-electric force gauge.

8. A calibrated impact hammer comprising:
a positioner;
a striker axially movable in the positioner, the striker comprising a striker inner end; and
a force gauge axially movable in the positioner, the force gauge comprising a force gauge inner end, the force gauge inner end being in communication with the striker inner end,
wherein the positioner and the striker together define a fluid passage axially therethrough such that fluid flows one of through and around the striker.

9. The calibrated impact hammer according to claim 8, wherein the force gauge comprises a force gauge outer end, the calibrated hammer further comprising at least one of a first pulse shaping tip in communication with the striker inner end and the force gauge inner end and a second pulse shaping tip in communication with the force gauge outer end.

10. The calibrated impact according to claim 9, wherein the calibrated hammer further comprises a strike plate in communication with the striker inner end and the first pulse shaping tip.

11. The calibrated impact hammer according to claim 8, wherein the positioner comprises one of a fixed tip and a plurality of interchangeable tips to ensure contact between the positioner and the structure.

12. The calibrated impact hammer according to claim 8, wherein the calibrated impact hammer further comprises one of a mechanical actuator and an electrical actuator connected to the striker, wherein said applying the striker step comprises actuating one of the mechanical actuator and the electrical actuator.

13. The calibrated impact hammer according to claim 8, further comprising:
providing a processor;
providing at least one vibration sensor communicating with the processor and the force gauge, the at least one vibration sensor measuring the vibration characteristics of the underwater structure.

14. The calibrated impact hammer according to claim 8, wherein the force gauge is waterproofed and is one of a strain gauge-type force gauge and a piezo-electric force gauge.

\* \* \* \* \*